US006468239B1

(12) United States Patent
Mollura, Sr. et al.

(10) Patent No.: US 6,468,239 B1
(45) Date of Patent: Oct. 22, 2002

(54) ORTHOTIC DEVICE

(75) Inventors: Carlos A. Mollura, Sr., Monrovia; Kenneth Rehm, Escondido, both of CA (US)

(73) Assignee: Vinyl Technology, Inc., Monrovia, CA (US)

( * ) Notice: Subject to any disclaimer, the term of this patent is extended or adjusted under 35 U.S.C. 154(b) by 0 days.

(21) Appl. No.: 09/616,656

(22) Filed: Jul. 14, 2000

(51) Int. Cl.[7] .................................................. A61F 5/00
(52) U.S. Cl. .............................. 602/23; 128/882; 5/648
(58) Field of Search ............................... 602/5, 13, 23, 602/27; 128/846, 882; 5/648, 650

(56) References Cited

U.S. PATENT DOCUMENTS

| | | | | |
|---|---|---|---|---|
| 5,328,445 A | * | 7/1994 | Spahn | 602/13 |
| 5,489,259 A | * | 2/1996 | Jacobs | 602/13 |
| 5,603,690 A | * | 2/1997 | Burry | 602/13 |
| 5,618,263 A | * | 4/1997 | Alivizatos | 128/882 |
| 5,957,874 A | * | 9/1999 | Klein | 602/23 |

* cited by examiner

Primary Examiner—Michael A. Brown
(74) Attorney, Agent, or Firm—Patrick F. Bright; Bright & Lorig (57) ABSTRACT

Calf supporting device includes a U-shaped or O-shaped support and, within the support, and attached to its inner surface, sealed bags at least partly filled with cushioning material to suspend a user's heel. The device also includes a foot pad at the end from which a user's foot protrudes for placement against, and support of the sole of a user's protruding foot.

17 Claims, 8 Drawing Sheets

ORTHOTIC DEVICE

This invention relates to an article of manufacture, namely, a calf, ankle and foot orthotic support device for men, women and children that allows the heel to float or be suspended, provides compression to the leg, and provides support for the foot. These articles are lower extremity management systems, and are sometimes called ankle/foot orthotics (AFO). As used herein, the terms "orthotic device" and "orthotic support device" mean an apparatus used to support, align, prevent, or correct deformities. This device includes a rigid, U-shaped or O-shaped support member, or a flexible support member that, in use, assumes an O-shape or a U-shape. These support members have a plurality of bags mounted inside the support member. These bags are at least partially filled with cushioning material such as particulates or natural fiber.

In a first embodiment, this device comprises a rigid, preferably thin-walled, U-shaped shell. Within this shell is a U-shaped block of sufficient thickness, rigidity, and flexibility to support the ankle, foot and heel of a user. Preferably, the U-shaped block is attached to the inner surface of the shell.

The shell is preferably made of a plastic such as a polycarbonate, ABS, or another plastic material. The shell is preferably about five to about twenty inches in length, about ten to about twenty-five inches in width, and about one-sixteenth of an inch to about five-sixteenths of an inch in thickness. In preferred embodiments, the shell is about three to about six inches longer than the U-shaped block at one end of the block.

The U-shaped block is preferably made of a foamed plastic such as cross-linked polyethylene, and may have a thickness ranging from about two to about four inches, at its thickest dimension, to about one-half inch to about two inches at its thinnest dimension. The inner profile of the block is U-shaped. Its outer profile is also U-shaped, terminating at the upper edges of the block in inwardly tapering or straight surfaces. The degree of taper from the legs of the U-shaped block is in the range of about twenty-five percent to about seventy-five percent.

Within this U-shaped block, and attached to its inner surface, are one or more scaled bags, preferably sealed fabric bags, at least partially filled with cushioning material. Preferably, these bags extend over substantially the entire length of the U-shaped block. The bags are wide enough to form a U-shaped or O-shaped supporting surface for the calf and ankle. The bags are preferably made of a material such as Spandex or another sturdy elasticized fabric.

A second embodiment includes a U-shaped outer member preferably made of a foamed plastic, or a plurality of foamed plastic layers joined to one another. This outer U-shaped support member can vary in thickness from about one inch or more at one end to about 0.5 inch at the other end, and is preferably thicker at the bottom of the U-shaped member than at the top of the side walls forming the U-shape.

Within this outer foamed U-shaped member is a thinner, more rigid plastic sheeting layer, preferably having a uniform thickness from end-to-end, and from the bottom of the U-shape to the top. Preferably, this thickness is in the range of about one-sixteenth of an inch to about thirteen-sixteenths of an inch.

Atop this rigid plastic sheeting is another foamed member whose dimensions are similar to those of the outer foamed member(s). Like the outer foamed members, this member can include a plurality of pieces of foam laminated or otherwise joined together.

Attached to the inner surface of the first and the second embodiments are one or more sealed bags at least partly filled with a cushioning material such as particulate solids, feathers or fibers such as wool. Preferably, the sealed bags are generally tubular, are approximately the same length as the support member, and have a cross-sectional area in the range of about four to about twenty-five square inches. Where a plurality of bags are used, one or more bags may be attached to one another, and/or one or more may be unattached to others.

In some embodiments, there are at least three such bags, with one such bag at the bottom of the U-shaped member, and another along each inner side of the U-shaped member. Another bag, whether unattached to the others or attached to one of the side bags, is positioned to extend over the top of a user's calf when the user's calf is placed into the U-shaped member. In other embodiments, there may be five, six or more bags, with two or more bags attached to one another, and others unattached to any other bag.

Preferably, the cushioning materials are loose inside the bags, and comprise particulates such as styrofoam or other plastic beads, seeds or natural materials such as feathers or fibers. Where the cushioning material is styrofoam beads or seeds, these particulates preferably have a diameter of less than about one-eighth of an inch, preferably less than about three thirty-seconds of an inch. Their volume is smaller than the inner volume of the sealed bag to permit both movement of the cushioning material, and support for an ankle, foot, calf and/or heel resting on the outer surface of the bags, without substantial abrasion. Preferably, the volume is also sufficient to avoid ulceration, and/or ischemia in the ankle, foot or heel of a user. The cushioning material preferably occupies at least about thirty percent and up to about ninety-five percent of the inner volume of each sealed bag.

In other embodiments, the U-shaped support member is flexible and/or bendable. In such embodiments, the U-shaped member may include a plurality of tubular air bags joined edge-to-edge to form a structure similar to an air mattress. Attached to one surface of the air mattress are one or more support bags filled at least in part with the cushioning material. The bags may, but need not all be the same length. Some of the bags may be longer than others to provide better support to the ankle and foot. Other bags for use atop the calf of a user may be shorter.

In all embodiments, the devices include one or more straps, e.g. Velcro straps or webbing, to hold the support device to the foot and ankle of a user. In some embodiments, these straps pass over one or more sealed bags containing cushioning material placed atop a user's calf/lower leg resting within the support device, such that the straps hold the topmost bag firmly against the top of the user's calf/lower leg.

The straps may be attached to an inner or the outer surface of the device to removably or detachably secure the orthotic device to the lower leg of a user. With these straps, the device can be bound firmly to the calf of a user to provide compression.

In preferred embodiments, the support device also includes a foot pad that engages and supports the sole of a user's foot. Since a user's foot extends beyond the end of the support device, the foot is susceptible to foot drop, foot contracture, or both. The foot pad minimizes these undesirable results.

The foot pad itself is a foot-sized bag at least partially filled with cushioning material such as particulate solids, feathers or fibers such as wool. Preferably, at least about thirty-five percent of the volume of the bag is filled with such cushioning material. More preferably, at least about fifty percent of the volume of the bag is filled with such cushioning material. The foot pad also includes a stiffener on the side of the bag opposite the side that contacts the foot of a user. The stiffener can be made of firm duck, thermoplastics such as polyethylene, ABS, polypropylene or polycarbonate, or other rigid materials, and may be molded in a desired shape, e.g. the shape of the bottom of a user's foot. The foot pad may have a sleeve or pocket to permit insertion and removal of one or more stiffeners of differing sizes and shapes. The pocket or sleeve preferably includes, at its opening, a closure e.g. a Velcro closure to hold the stiffener in place in the sleeve or pocket. For example, an insertable stiffener may be shaped to conform to the base of a user's foot, and/or the stiffener may function like the sole of a shoe, thus permitting a user to be ambulatory.

The foot pad is attached to, and preferably separable from a supporting strap by fasteners such as Velcro and can be positioned along the strap to maximize a user's comfort.

BRIEF DESCRIPTION OF THE DRAWINGS

The invention can better be understood by reference to the drawings, in which.

DESCRIPTION OF THE PREFERRED EMBODIMENTS

Figures 1, 2:
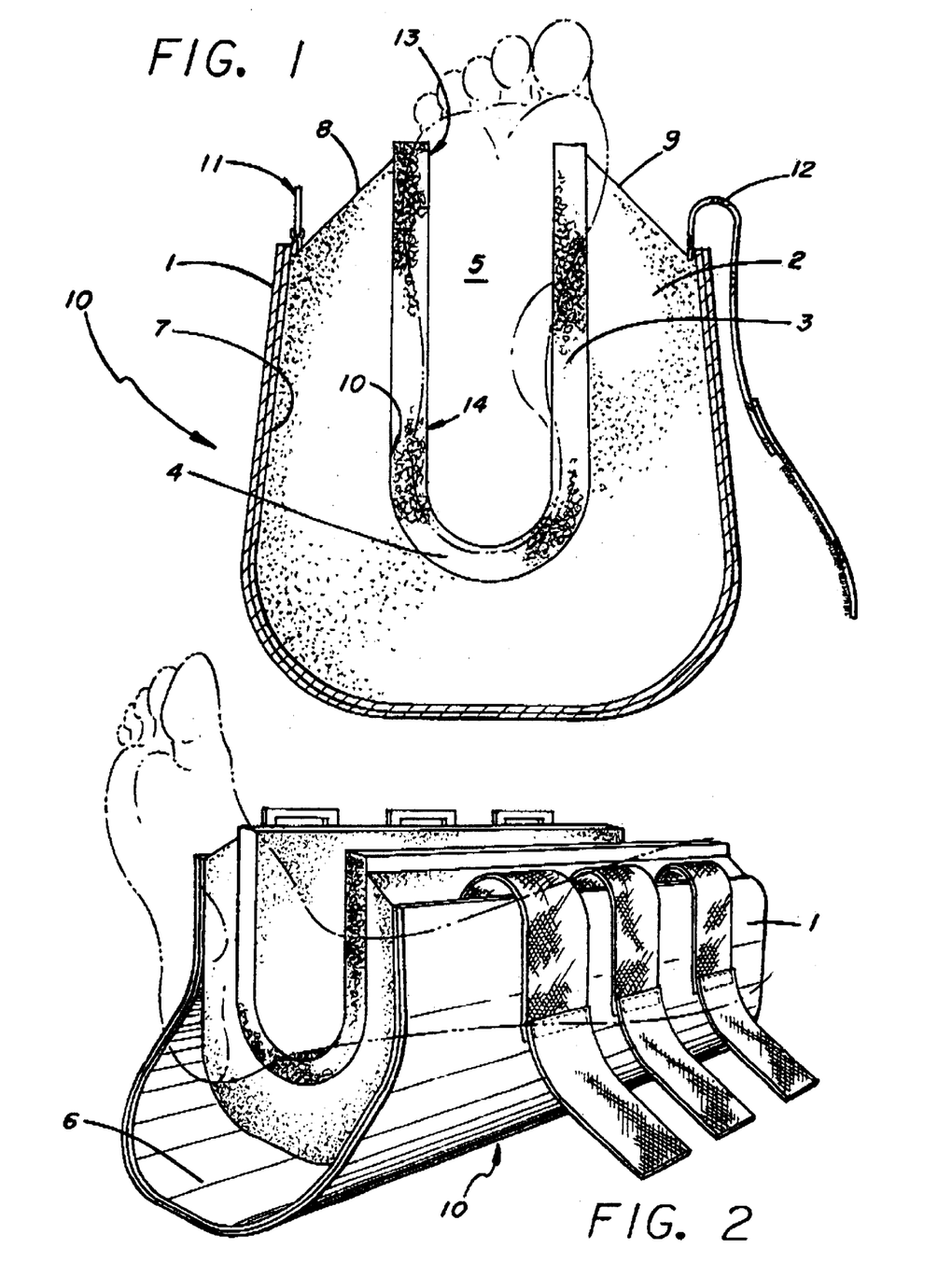
FIG. 1 shows an end elevation view of a first embodiment of the support device.
FIG. 2 shows a side elevation view of the embodiment of FIG. 1.

In FIGS. 1 and 2, orthotic device 10 includes outer, rigid, U-shaped shell 1. Shell 1 is made of ABS, and is about fifteen inches long, twenty inches wide, and about one-sixteenth of an inch in thickness. Attached to the inner wall surface 7 of shell 1 is block 2 made of cross-linked polyethylene foam. Block 2 is U-shaped, and is secured to the inner surface 7 of shell 1 by glue or otherwise. Block 2 has two inwardly tapering end surfaces 8 and 9 formed at approximately a forty-five degree angle to the plane of each leg of block 2. Attached to the inner surface 10 of block 2 is sealed bag 3 made of Spandex and partially filled with styrofoam beads 4. Sealed bag 3 is about one inch wide, about twelve inches long, and has a wall thickness of about one-thirty-seconds of an inch.

Inside bag 3, and filling about sixty percent of its inner volume, are styrofoam beads 4. Beads 4 are loose within bag 3. As FIG. 1 shows, foot 5 of a user can be placed within the U-shaped region 13 formed by the inner surface 14 of bag 3, with the heel of foot 5 projecting beyond the end of bag 3 onto extension 6 (see FIG. 2). Extension 6 is an integral part of shell 1, and is of a sufficient length to receive the user's heel.

Orthotic device 10 can be secured to foot 5 by Velcro or webbing straps 11 and 12. There may be more than one pair of such straps. In preferred embodiments, there are at least three such pairs of straps, spaced along the length of shell 1.

Figure 3:
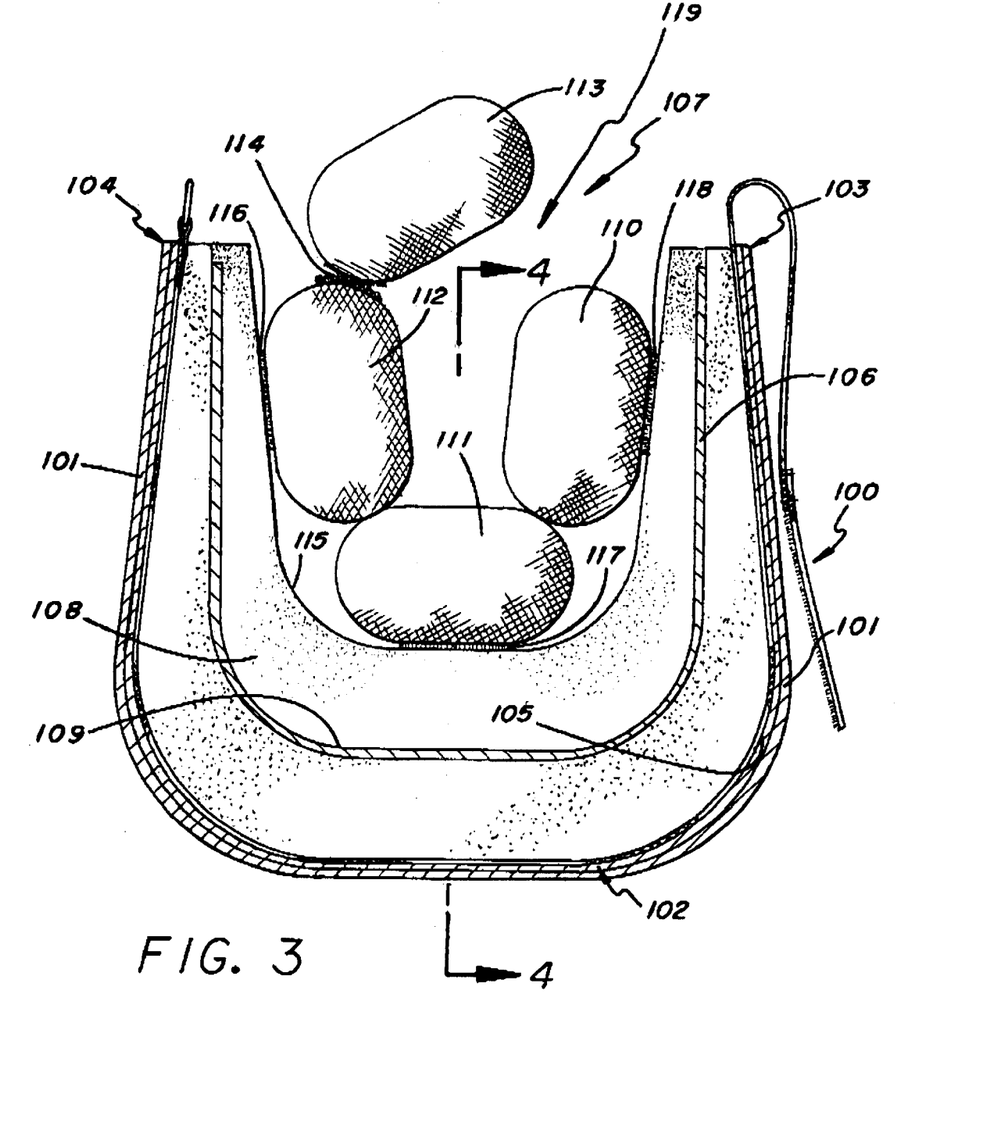
FIG. 3 shows an end elevation view of a second embodiment of the heel support device.
Figure 4:
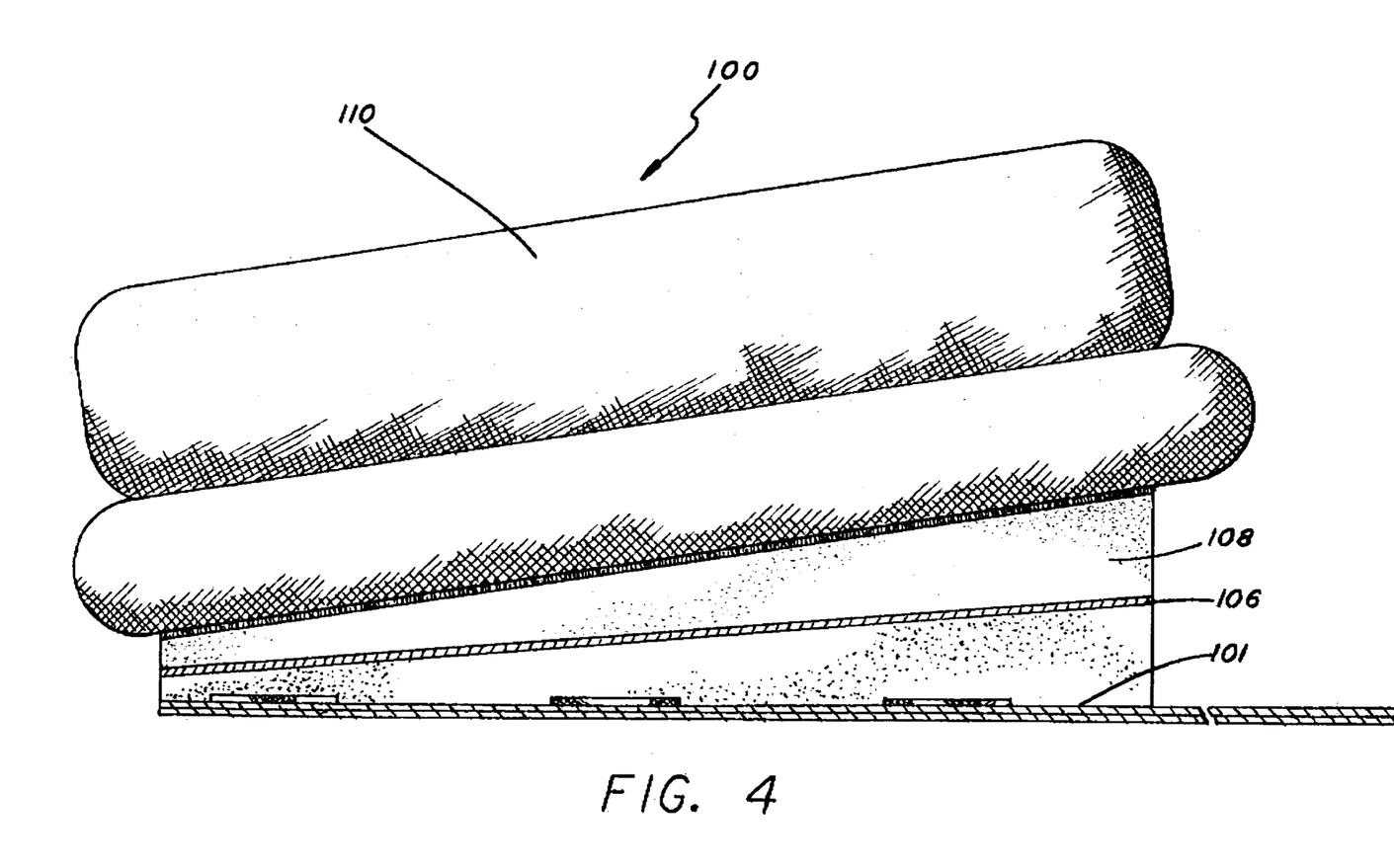
FIG. 4 shows a side elevation view in cross-section, taken on line 3—3 of FIG. 3, of the embodiment shown in FIG. 3.

FIGS. 3 and 4 show a second embodiment 100 of the support device. This embodiment includes an outer, firm, soft, U-shaped shell 101, made of foamed cross-linked polyethylene. At proximal end 102, the thickness of shell 101 is about one inch. Shell 101 tapers at its distal end to a thickness of about one-quarter of an inch. Shell 101 also tapers to a thickness of about one-quarter of an inch at the upper ends of arms 103 and 104 of the U-shaped member. Shell 101 is about fifteen inches long, and eight inches wide.

Attached to inner wall surface 105 of shell 101 is rigid, plastic, U-shaped member 106, attached to surface 105 by glue or otherwise. Member 106 has a thickness in the range of about one-sixteenth to three-sixteenths of an inch, and provides rigidity to the device.

Attached to this rigid sheeting, or sandwiched between the sheeting 106 and shell 101, are a plurality of straps that extend over the top surface 107 of device 100 to hold the device to the calf/lower leg of a user.

Attached to the inner surface 109 of U-shaped member 106 is U-shaped foam member 108. The dimensions of this U-shaped member are approximately the same as those of U-shaped member 101. Member 108 can be made of the same material as shell 107, or of a different foam material. Member 108 may include slots to allow straps to pass through, and to secure the device atop a user's calf/lower leg.

Attached to the inner surface of member 108 are bags 110, 111, 112, and 113. Bags 112 and 113 are connected to one another along their length at junction 114. Bags 112, 111, and 110 are attached to the inner surface 115 of member 108 by glue or other means 116, 117, and 118. These bags are about twelve to about fifteen inches in length, about three to about five inches in diameter, and have a volume in the range of about seventy to about two hundred seventy cubic inches. Inside these sealed bags are particulates such as light styrofoam beads or natural matter such as feathers or seeds, occupying about thirty percent or more of the internal volume of each bag. The bags may all be of the same length, or may differ in length, depending on the support structure desired. The bags may also be joined to one another along their length, or may be unattached to one another.

In FIG. 3, bag 113 projects above the plane formed by the upper edges of device 100, and is positioned to lie atop the lower leg of a user positioned in space 119 formed by the inner surfaces 110, 111, and 112.

Figure 5:
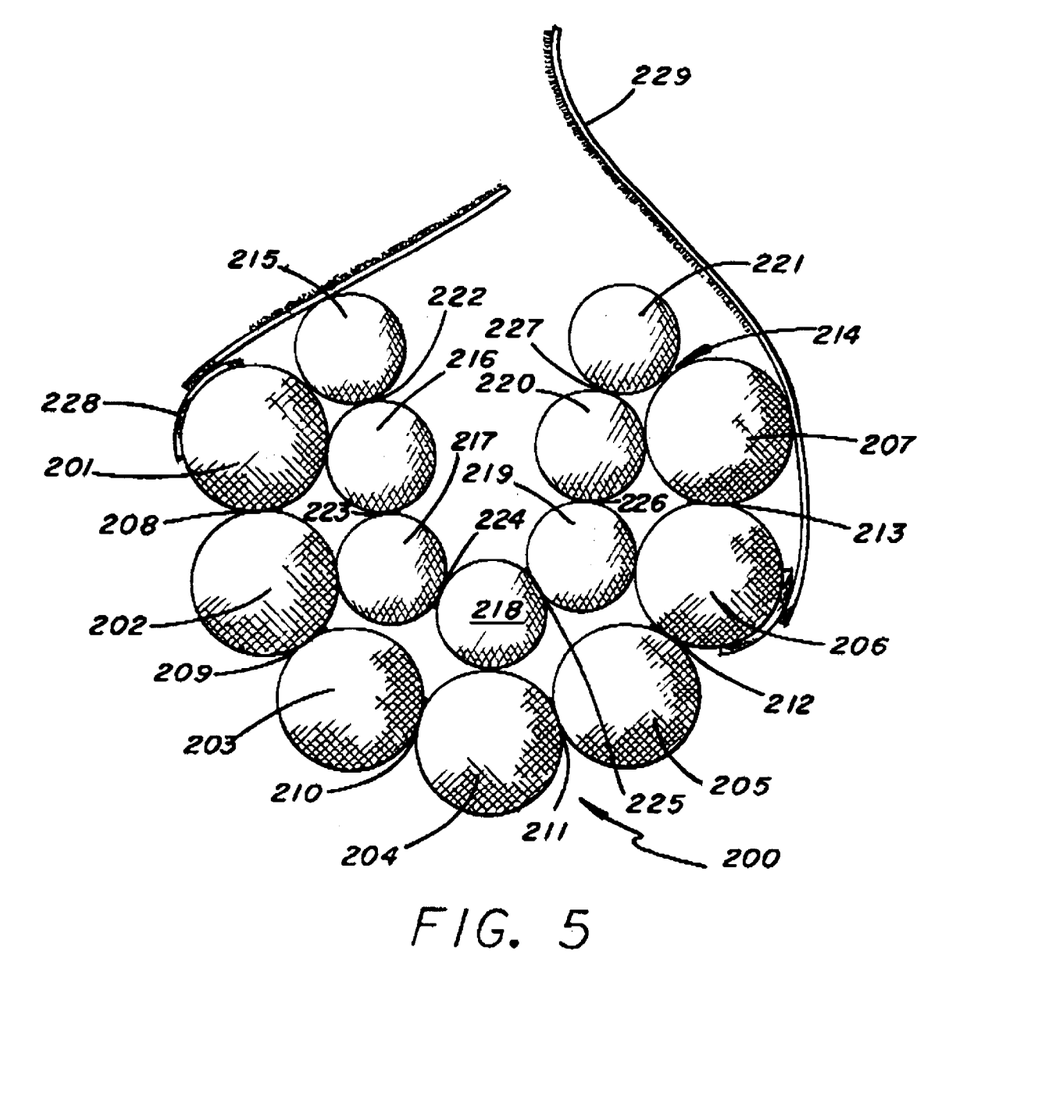
FIG. 5 shows an end elevation view of a third embodiment of the heel support device.
Figure 5A:
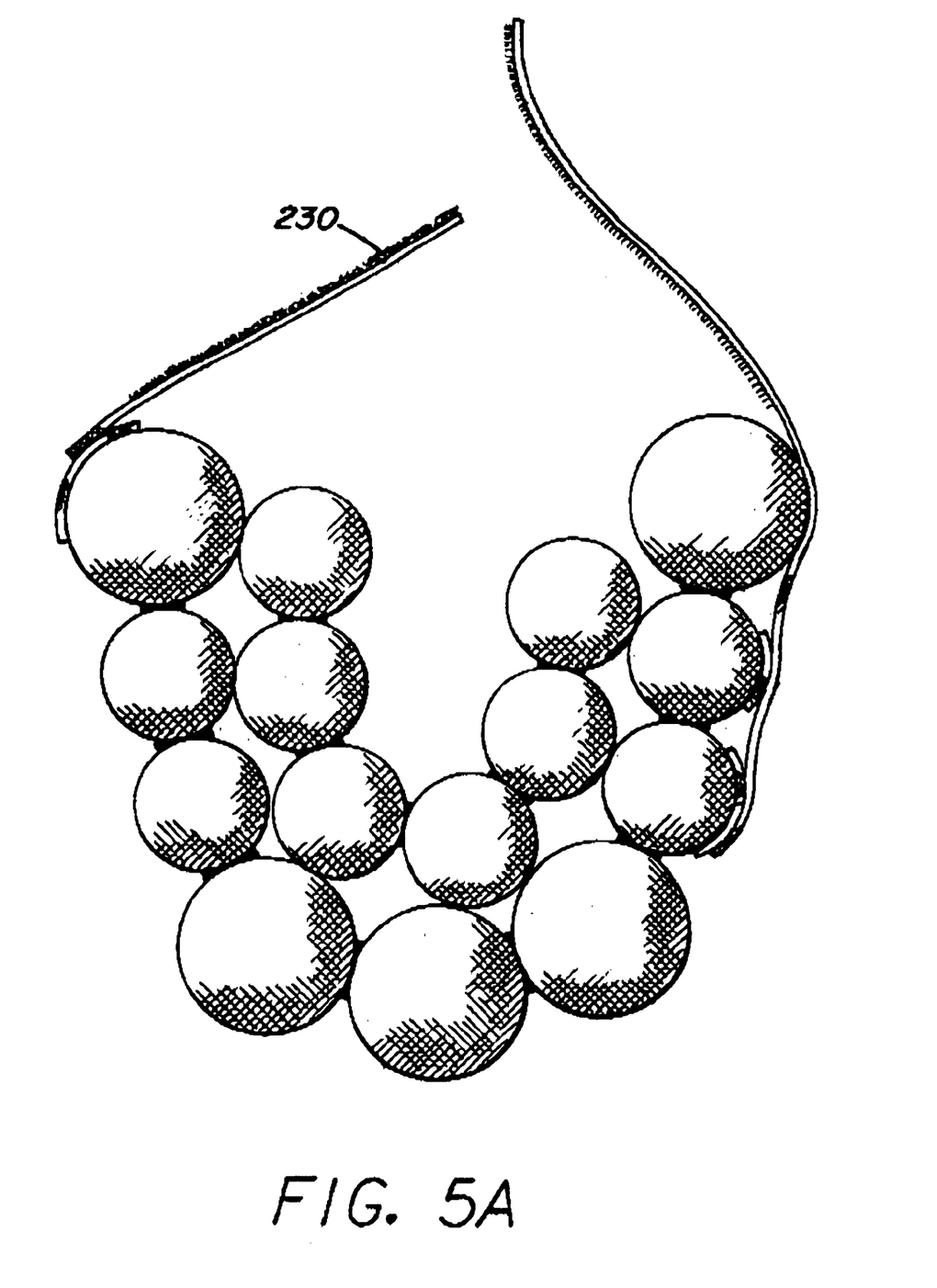

FIG. 5 shows a third embodiment 200 of a support device. U-shaped support is formed by gas-filled bags 201, 202, 203, 204, 205, 206, and 207. Some of these bags may be of substantially uniform cross-section from end-to-end. Others may taper from a first cross-section to a second, smaller cross-section along their length, with the larger cross-section at the end that supports, and elevates the calf, ankle and heel of a user. The support member may also taper in profile from the heel end to the opposite end, to minimize contact between a user's foot surfaces and the gas filled bags 201, 202, 203, 204, 205, 206 and 207.

Bags 201–207 are joined to one another along their length at contiguous surfaces 208, 209, 210, 211, 212, and 213. On inner surface 214 of device 200 are a plurality of fabric or plastic bags 215, 216, 217, 218, 219, 220, and 221, each filled to thirty percent of the bag's volume or more with cushioning particulates or natural matter. In structure, form, and content, these bags are similar to bags 110, 111, 112, and 113 in FIGS. 3 and 4. These bags may be unattached to one another, or may be joined to one another along contiguous surfaces 222, 223, 224, 225, 226, and 227.

Attached to ends 206/207 are straps 228 and 229. These straps are of sufficient length to overlap one another, and are attached to one another by Velcro, or another suitable connector, to hold device 200 under a user's foot and ankle. There may be additional bags unconnected to the device for placement over a user's calf/lower leg, and beneath straps 228 and 229, to provide additional cushioning under a user's foot. The bags 215–221 may be of the same length, size and shape, or can differ from one another in length, size and shape, depending on the desired support structure.

Figure 6:
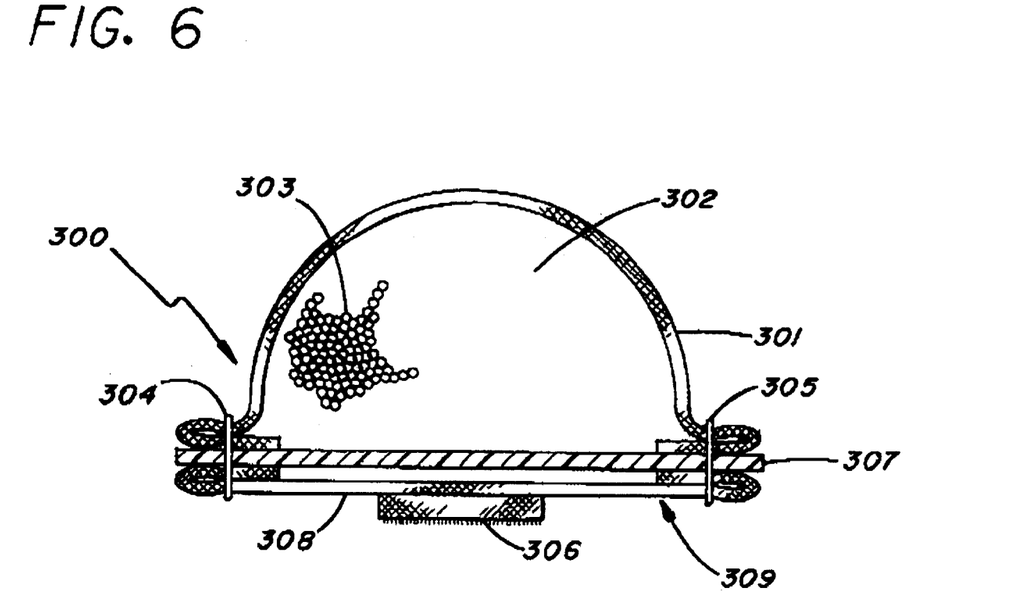
FIG. 6 shows a first embodiment of a foot pad including an internal stiffener that attaches, removably, to a strap for securing the foot pad over the sole of a user's foot.

FIG. 6 shows a first foot pad embodiment 300 including a top, foot-contacting, fabric piece 301, a bottom fabric piece 308, and, between fabric pieces 301 and 308, internal, rigid stiffener 307, here made of a thermoplastic such as ABS. The first and second pieces 301 and 308 of foot pad 300 are held together, with stiffener 307 between them, by seams 304 and 305. Within the space formed between stiffener 307 and fabric piece 301 is cushioning material, here beads 303. These beads fill more than seventy-five percent of this space. Attached to the bottom surface 309 of fabric piece 308 is Velcro pad 306. Velcro pad 306 permits attachment of footpad 300 to strap 230 shown in FIG. 5. (CAM: Please add a strap 230 to FIG. 5).

Figure 7:
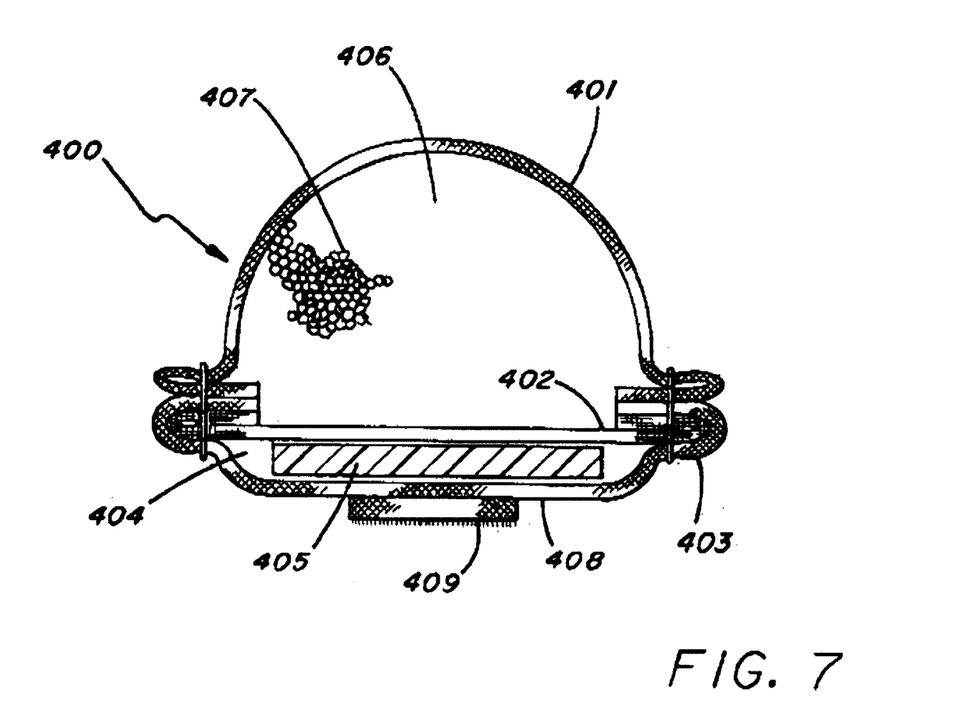
FIG. 7 shows a second embodiment of such a foot pad, including a sleeve for insertion and removal of internal stiffeners of differing sizes and shapes.

FIG. 7 shows a second foot pad embodiment 400. Foot pad 400 includes first fabric piece 401, second fabric piece 402, and third fabric piece 403. Fabric pieces 402 and 403 form a sleeve or pocket 404 in which a stiffener 405 of desired shape and size can be inserted. Within space 406 formed between fabric pieces 401 and 402 are cushioning material 407, here beads, which fill more than fifty percent of the volume in this space. Attached to the bottom surface 408 of foot pad 400 is Velcro pad 409. Velcro pad 409 permits attachment of foot pad 400 at a desired location along strap 230, shown in FIG. 5.

Figure 8:
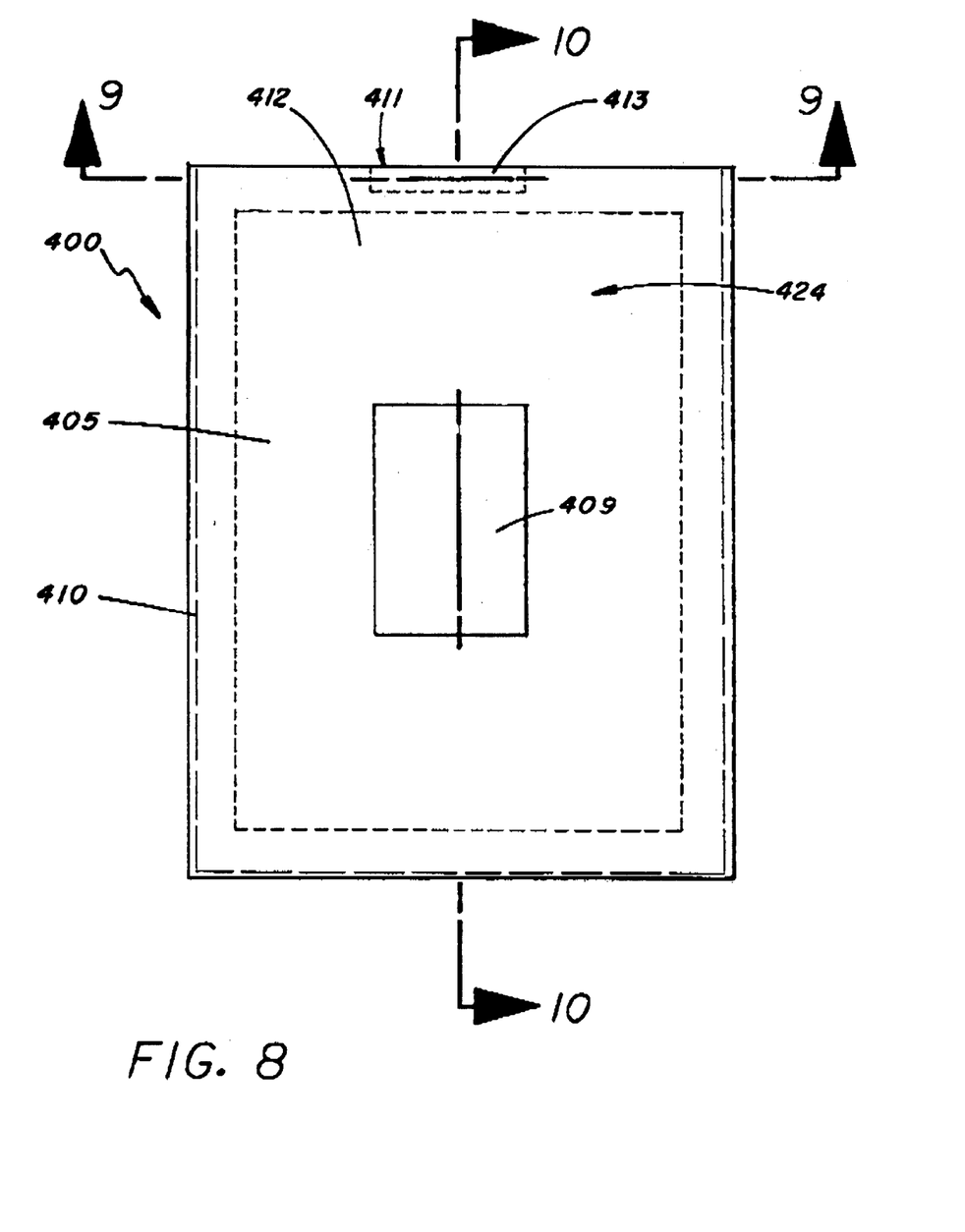
FIG. 8 shows a bottom plan view of the second foot pad embodiment shown in FIG. 7.

FIG. 8 shows a bottom plan view of foot pad 400. Seam 410 forms three sides of a pocket 412 with an entrance or opening to the pocket at 411. Velcro pad 413, near the entrance to sleeve 412, along with a complementary facing Velcro pad (see FIG. 9), provides a closure to hold a stiffener within sleeve 404.

Figure 9:
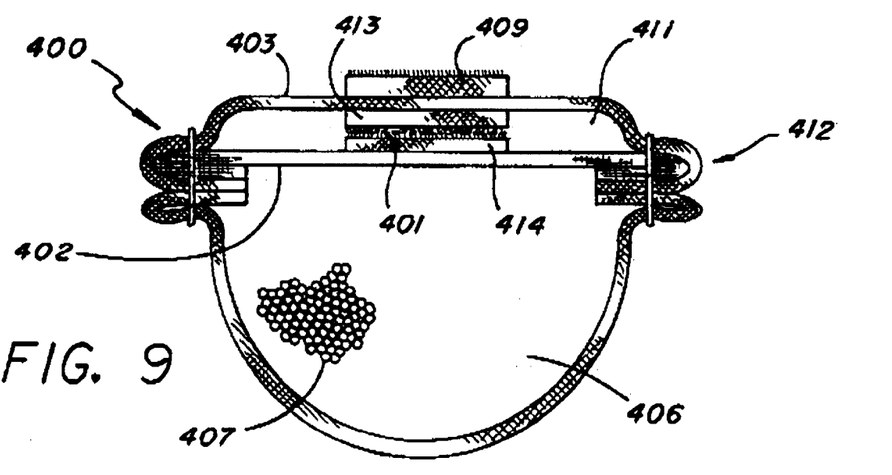
FIG. 9 shows a cross-sectional view of the foot pad embodiment of FIG. 8, taken on line A—A on FIG. 8.
Figure 10:
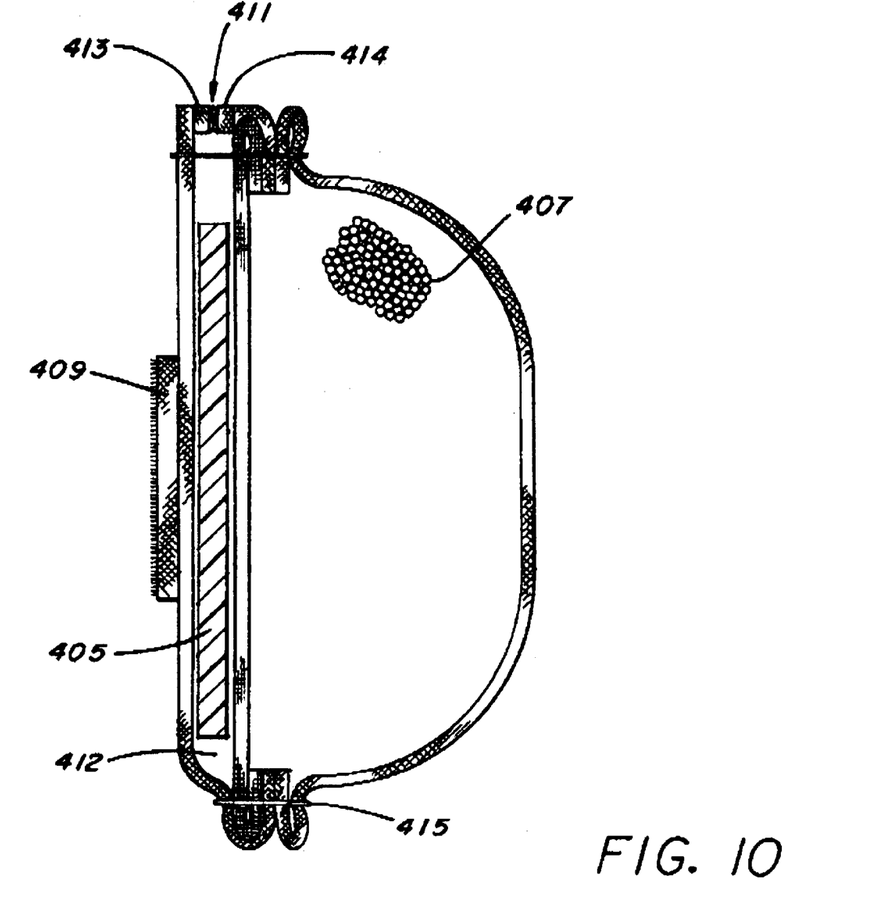
FIG. 10 shows a cross-sectional view of the foot pad embodiment of FIG. 8, taken on line B—B of FIG. 8.

FIGS. 9 and 10 show cross-sectional views of the foot pad 400 taken on lines A—A and B—B, respectively, in FIG. 8. FIG. 9 shows opposing Velcro pads 413 and 414 at the entrance 411 to sleeve 404 that hold a stiffener in sleeve 404 when attached to one another.

What is claimed is:

1. An orthotic device that floats or suspends the heel of a user comprises a rigid, U-shaped or O-shaped, thin-walled member;
   attached to the inner surface of said member a U-shaped block or O-shaped block of sufficient thickness, rigidity and flexibility to support the ankle, foot and heel of said user; and
   attached to the inner surface of said U-shaped block or O-shaped block, a plurality of sealed bags comprising inner volumes at least partly filled with a loose cushioning material, said bags extending along substantially the entire length of said U-shaped or O-shaped member.

2. The device of claim 1 wherein said rigid, U-shaped or O-shaped, thin-walled member includes a U-shaped or O-shaped portion extending beyond the end of said U-shaped block or O-shaped block, said portion having a sufficient length and width to preclude the foot and ankle of a user from making contact with any other object.

3. The device of claim 1 or claim 2 further comprising at least two straps attached to the upper end of said rigid, U-shaped or O-shaped, thin-walled member, and positioned to secure said orthotic device to the calf/lower leg of a user when said calf/lower leg is placed into the U-shaped or O-shaped region formed by the inner surfaces of said sealed bags.

4. An orthotic device that supports the calf of a user comprises:
   a flexible member that forms a U-shape or O-shape in use;
   attached to the inner surface of said member, one or more sealed bags comprising inner volumes at least partly filled with a loose cushioning material with a sufficient number of bags extending along said member to support said calf.

5. The device of claim 4 wherein said member forming a U-shape or O-shape comprises:
   a plurality of air-tight tubular members joined to one another at contiguous surfaces to form a flexible member that forms a U-shape or O-shape in use, and, attached to the inner surface of said member, at least three of said sealed bags;
   said device including straps to attach said device to the calf of said user.

6. The device of claim 5 wherein said air tight tubular members are made of flexible fabric that can conform to the foot and calf of said user.

7. The device of claim 6 wherein said air tight tubular members are made of flexible fabric that can conform to the foot and calf of said user.

8. The device of claim 4 wherein from about thirty percent to about ninety-five percent of the volume of each of said bags is filled with said loose cushioning material and wherein said loose cushioning material is selected from the group consisting of fibers, feathers, seeds and plastic beads.

9. The device of claim 1 or claim 4 further comprising strap means at the end of the device from which a user's foot protrudes, and a foot pad attachable to and detachable from said strap means, said strap means permitting attachment of said foot pad to the sole of a user's foot at a desired position on said strap means.

10. The device of claim 9 wherein said foot pad comprises a sealed bag with an inner volume at least partly filled with a loose cushioning material, said bag including a stiffener of desired size and shape inside said bag, and a connector for attachment of said bag to said strap.

11. The device of claim 4 further comprising of plurality of said sealed bags.

12. The device of claim 4 wherein said member that forms a U-shape or O-shape in use comprises a plurality of air tight tubular members joined to one another at contiguous surfaces and, attached to the inner surface of said member, at least 2 of said sealed bags.

13. An orthotic device that floats or suspends the heel of a user comprises a rigid, U-shaped or O-shaped, thin-walled member; attached to the inner surface of said member, a U-shaped block or O-shaped block of sufficient thickness, rigidity and flexibility to support the ankle, foot and heel of said user, said member including a U-shaped or O-shaped portion extending beyond the end of said U-shaped block or O-shaped block, said portion having a size sufficient to minimize contact of the foot and ankle of the user with any other object; and     attached to the inner surface of said U-shaped block or O-shaped block, a plurality of sealed bags comprising inner volumes at least partly filled with a loose cushioning material, with a sufficient number of bags extending along said U-shaped or O-shaped member to support said calf.

14. An orthotic device that supports the calf of a user comprises:

a rigid member that forms a U-shape or O-shape in use;

attached to the inner surface of said member, a plurality of sealed bags, each of said bags comprising inner volumes at least partly filled with a loose cushioning material, with a sufficient number of bags extending along said member to support said calf.

15. The device of claim 14 wherein from about thirty percent to about ninety-five percent of the volume of each of said bags is filled with said loose cushioning material and wherein said loose cushioning material is selected from the group consisting of fibers, feathers, seeds and plastic tends.

16. The device of claim 14 or claim 13 further comprising strap means at the end of the device from which a user's foot protrudes, and a foot pad attachable to and detachable from said strap means, said strap means permitting attachment of said foot pad to the sole of a user's foot at a desired position on said strap means.

17. The device of claim 16 wherein said foot pad comprises a sealed bag with an inner volume at least partly filled with a loose cushioning material, said bag including a stiffener of desired size and shape inside said bag, and a connector for attachment of said bag to said strap.

* * * * *